Figure 1:
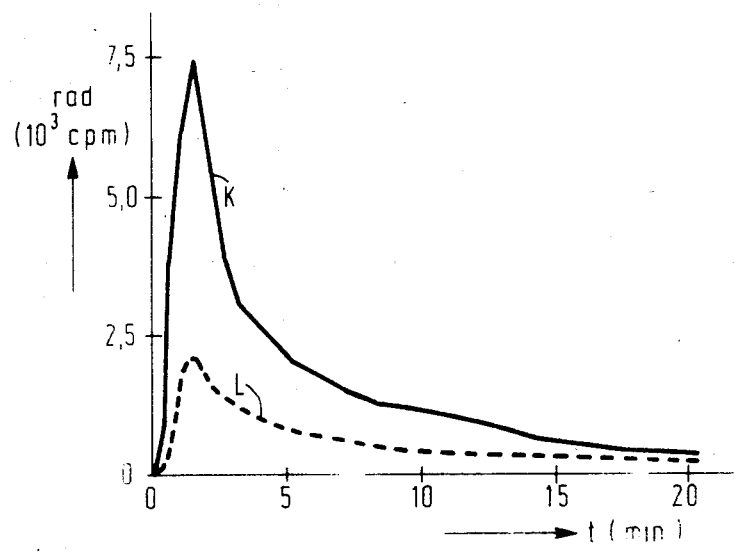
Figure 2:
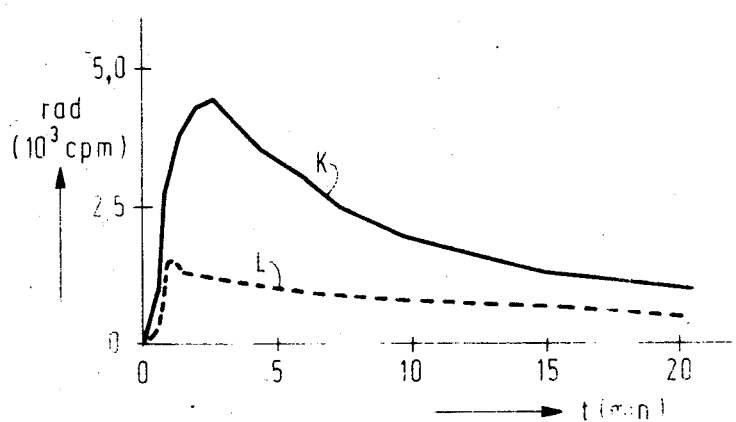

United States Patent [19]

Wenzel et al.

[11] Patent Number: 4,584,186
[45] Date of Patent: Apr. 22, 1986

[54] RADIOLABELLED METALLOCENE DERIVATIVES

[75] Inventors: Martin Wenzel; Gert Schachschneider, both of Berlin, Fed. Rep. of Germany; Jan Nielsen, Le Petten, Netherlands

[73] Assignee: Mallinckrodt, Diagnostica (Holland) B.V., Betten, Netherlands

[21] Appl. No.: 554,495

[22] Filed: Nov. 22, 1983

[30] Foreign Application Priority Data

Dec. 1, 1982 [DE] Fed. Rep. of Germany ....... 3244886

[51] Int. Cl.$^4$ ...................... A61K 29/00; A61K 49/00
[52] U.S. Cl. ........................................ 424/1.1; 534/10; 556/136; 556/142; 556/60; 424/9
[58] Field of Search .............. 424/1.1, 9; 260/429 CY, 260/429 J, 438.5 R, 439 R

[56] References Cited

U.S. PATENT DOCUMENTS 4,028,389 6/1977 Wenzel et al. ........................ 424/1.1

FOREIGN PATENT DOCUMENTS 2246460 4/1974 Fed. Rep. of Germany ....... 424/1.1

OTHER PUBLICATIONS

Langheim et al., *Chem. Ber*, 108(1975) 146–154.
Schachschneider et al., *J. Label. Comp. Radiopharm.* 19(1982) 1071–1079.
Wenzel et al., *Z. Naturforschung*, 32C (1977), 473–481.
Stadlbauer et al., *J. Label. Comp. Radiopharm.* 13(1977) 491–508.

*Primary Examiner*—Christine M. Nucker
*Attorney, Agent, or Firm*—R. J. Klosterman; L. N. Goodwin

[57] ABSTRACT

The invention relates to radiolabelled metallocene derivatives of the general formula

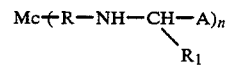

wherein Mc is a metallocenyl group with a radioactive central atom, R is a carbonyl or methylene group, $R_1$ is a hydrogen atom or an alkyl group having 1–4 carbon atoms, A is a carboxy group or a pharmaceutically acceptable salt thereof, or an alkoxycarbonyl or alkanoyl group having 2–5 carbon atoms, and n is 1–4.

The invention also relates to radiodiagnostic compositions comprising said radiolabelled metallocene derivatives and to a method of performing a radiodiagnostic examination, in particular of examining the renal function.

26 Claims, 5 Drawing Figures

RADIOLABELLED METALLOCENE DERIVATIVES

The invention relates to radiolabelled metallocene derivatives, to radiodiagnostic compositions to be used particularly for examining the renal function, and to the use of said compositions.

Radionuclide-labelled compounds may be used for diagnostic examination, e.g., deviations in the shape and function of internal organs and the presence and location of pathological processes in the body. For this purpose, a composition in which the radioactive compound is present, may be administered to the patient, for example, in the form of an injectable liquid. By means of suitable detection devices, e.g. a gamma camera, images can be obtained by recording the emitted radiation of, for example, the organ, the body fluid or the pathological process in which the radioactive compound is incorporated.

There is a permanent need for easily available radiodiagnostic compositions suitable for examining the renal function, especially for patients after transplantation of a kidney or after large vascular operations, and for victims of accidents. For this purpose often the easily available iodohippuric acid sodium salt labelled with iodine-131 is used. Iodine-131, however, is not an ideal radioisotope in nuclear medical applications, because its emission of $\beta$ particles leads to an excessive body burden of radiation. Therefore, the amount of radioactivity administered must be low, and as a consequence, less reliable information will be obtained. In addition, the radiation characteristics of iodine-131 are unfavorable in that its high-energy gamma radiation, viz 365 keV, causes poor spatial resolution and counting efficiency in recording the emitted radiation. Finally, due to the comparatively long half-life of approximately 8 days, iodine-131 labelled compounds are less suited for examining the renal function, because when the kidney function is impaired, the residence time of the diagnostic is increased. Therefore, in recent years, hippuran labelled with iodine-123 is proposed for examining the renal function, because iodine-123 does not present the above disadvantages as to radiation characteristics. Iodine-123, however, has a relatively short half-life, viz. approximately 13 hours, so that logistical problems arise after cyclotron production of said isotope.

It is the object of the invention to provide radiodiagnostic compositions to be used particularly for examining the renal function, comprising labelled compounds which on the one hand have the favorable properties of labelled hippuran, but on the other do not present the above disadvantages as to burden of radiation and availability.

According to the invention this object can be achieved by providing radiodiagnostic compositions, comprising radiolabelled metallocene derivatives of the general formula

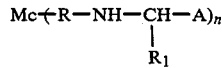

wherein
Mc is a metallocenyl group with a radioactive central atom,
R is a carbonyl or methylene group,
$R_1$ is a hydrogen atom or an alkyl group having 1–4 carbon atoms,
A is a carboxy group or a pharmaceutically acceptable salt thereof, or an alkoxycarbonyl or alkanoyl group having 2–5 carbon atoms, and n is 1–4.

In principle, radionuclides of metals suitable for the formation of metallocenes can be used as central atoms, provided that these radionuclides have favorable properties as to half-life and radiation characteristics. Because of their excellent binding characteristics in the metallocene molecules, radionuclides of the metals iron, ruthenium, osmium, chromium, vanadium, and cobalt are preferred as central atoms. Of these radionuclides, ruthenium-97 is preferable as far as half-life and radiation characteristics are concerned. As a matter of fact, this radionuclide is an ideal radionuclide for radiodiagnostic applications because of its gamma energy of 215 keV, its half-life of 2.9 days and its absence of B emission. Therefore, ruthenocenes which are radiolabelled with ruthenium-97 are to be considered as particularly suitable in radiodiagnostic compositions, especially when used for examining the renal function. These preferred ruthenocene derivatives have the general formula.

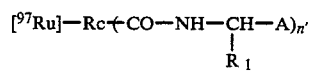

wherein
$[^{97}Ru]$—Rc is a ruthenocenyl group radiolabelled with ruthenium-97,
A has the meanings given in claim 1,
$R'_1$ is a hydrogen atom or a methyl group, and
$n'$ is 1 or 2.

Of the above compounds ruthenium-97 labelled ruthenocenoyl glycine and 1,1'-diglycine are preferred.

Metallocenes and metallocene derivatives having a radioactive central atom are known from literature, e.g. from U.S. Pat. No. 4,028,389. Although this patent specification particularly relates to a process for the production of labelled metallocenes, an experiment is described wherein ruthenium-103 labelled ruthenocene and ruthenocene monocarboxylic acid amide are used for organ distribution studies in rats; these studies are intended to show that the compounds tested may be used for examining liver and lungs. The figures accompanying this specification clearly show that these ruthenocenes are not suitable for examining the renal function, because of their insufficient organ specificity. The radioactivity accumulates in the lung and in the liver in at least equal amounts as in the kidney. In addition, to be suitable for examining the renal function, a sufficiently fast clearance from the blood via the kidneys is required. The renal clearance is a measure of the purification of the blood plasma by the kidneys. There is not any indication in said U.S. patent that the ruthenocenes, which behavior in rat organs is described, would present a sufficient renal clearance.

Surprisingly it has been found, however, that the radiolabelled metallocene derivatives of the invention have a fast renal clearance, and consequently are very suitable for examining the renal function, especially for determining the effective renal plasma flow. As a matter of fact, it has proven that the clearance of ruthenocenoylglycine labelled with radioactive ruthenium is even faster than that of iodohippuric acid sodium salt labelled with iodine-125, as will be apparent from the examples.

The radiolabelled metallocene derivatives of the present invention are new compounds which may be prepared in a manner known in the art for the preparation of related compounds. Preferably, the compounds of the invention having the general formula

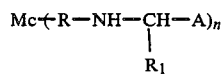

wherein the symbols have the above meanings, are prepared by reacting a non-radioactive metallocene derivative with a radioactive metal compound. This method has been described for the preparation of related metallocene derivatives in the before-mentioned U.S. Pat. No. 4,028,389. The process is carried out at increased temperature, preferably at 30° C.–250° C. The reaction can be carried out in a suitable polar organic solvent, like ethanol or dimethylformamide, or without a solvent. The latter reaction can be improved by suitable additives, e.g. aluminium oxide or N,N-dimethylaniline, as described by Schneider, Wenzel and Riesselmann in *J. Lab. Compds. Radiopharm.* XV, 1978, 295–307, for related metallocenes. In the starting non-radioactive metallocene derivatives the central metal atom is preferably iron, cobalt, nickel, chromium, vanadium, ruthenium, osmium or another suitable metal; ferrocene derivatives are generally used as starting materials. The starting radioactive metal compounds are preferably salts, e.g. halides, of the desired radionuclides. The radiolabelled metallocene derivatives of the above general formula so obtained can be modified, if desired, by a simple subsequent reaction. By such a reaction a carboxy group can be converted into a salt or ester thereof with the aid of a suitable base or alcohol respectively; alternatively, a salt or an ester can be hydrolyzed, if desired, yielding the corresponding carboxylic acid.

The present invention also relates to radiodiagnostic compositions comprising in addition to the above defined radiolabelled metallocene derivatives pharmaceutically acceptable formulation liquids or vehicles. As a formulation liquid preferably physiological saline is used. If desired, auxiliary substances may be added, e.g. buffers like tris(hydroxymethyl)aminomethane (TRIS) or a phosphate buffer, and/or stabilizing substances.

It is preferred to incorporate into the radiodiagnostic compositions inactive carriers or loads. When the compositions are intended for examining the renal function these inactive carriers should be selected from substances having a fast renal clearance. Such inactive carriers are, for example, substituted or unsubstituted hippuric acid derivatives, like o-iodohippuric acid, p-aminohippuric acid, and the salts thereof, or suitable metallocene derivatives. Suitable metallocene derivatives are metallocenes having one or more R—NH—CHR$_1$—A groups, wherein R, R$_1$ and A have the meanings defined before, such as inactive ruthenocenoyl glycine or derivatives thereof or the more economical corresponding ferrocenoyl compounds.

Inactive ruthenocenoylglycine and derivatives thereof are new compounds which may be prepared in a known manner for the preparation of related compounds.

These new compounds, having the general formula

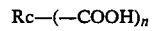

wherein Rc is ruthenocenyl group, and R, R$_1$, A and N have the above meanings, can be prepared, for example, (1) if R is a carbonyl group, by reacting a compound of the general formula

wherein Rc and n have the above meanings, after conversion into the corresponding acid chloride, with an amine of the general formula $H_2N—CHR_1—A'$ wherein R$_1$ has the above meaning, and A' is an alkoxycarbonyl or alkanoyl group having 2–5 carbon atoms, or (2) if R is a methylene group, by converting ruthenocene into a compound of the general formula

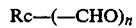

wherein the symbols have the above meanings, by using the well-known Vilsmeyer reaction, followed by reacting the aldehyde so obtained with an amine with the general formula

wherein the symbols have the above meanings, and which latter reaction is carried out in the presence of a reducing substance, after which the compound obtained, wherein A' is an alkoxycarbonyl or alkanoyl group, can easily be converted into the corresponding acid or salt by a saponification reaction. Said saponification reaction is preferably carried out in a polar organic solvent like ethanol, with a suitable base like sodium hydroxide, and at a reaction temperature between 0° C. and the boiling point of the solvent. The amination reaction mentioned under (1) is preferably carried out in a polar organic solvent, for example an ether like tetrahydrofuran, at a temperature between 0° C. and the boiling point of the solvent. The starting acid chloride can be obtained from the corresponding acid with a suitable chlorination agent like PCl$_5$, POCl$_3$ or SOCl$_2$.

The reductive amination mentioned under (2) is preferably carried out in a suitable polar organic solvent, for example an alkanol like methanol, at a reaction temperature between 0° C. and the boiling point of the solvent, and in the presence of a reducing substance like NaBH$_4$ or NaCNBH$_3$.

For carrying out a radiodiagnostic examination, a radiodiagnostic composition as defined above, if desired after dilution with a liquid which is acceptable to the body, e.g. physiological saline, may be administered to a warm-blooded living being in a quantity from 100 uCi to 5 mCi, preferably from 0.5 to 2 mCi per 70 kg of body weight, after which the radioactive radiation emitted by the living being is recorded. So the invention also relates to a method of subjecting a warm-blood living being in particular a human being, to a nuclear diagnostic examination. For recording the emitted radiation a suitable detector is used, for gamma rays for example a gamma camera.

The invention will now be described in greater detail with reference to the following specific examples.

EXAMPLE I

Preparation of ruthenocenoyl ethylglycinate, labelled with ruthenium-103; formula: [$^{103}$Ru]—Rc—CO—NH—CH$_2$—COOC$_2$H$_5$ Ferrocenoylethylglycinate (Fc—CO—NH—CH$_2$—COOC$_2$H$_5$) in an amount of 7 mg was placed in a glass ampoule and 300 ul of an ethanolic solution of ruthenium-103 trichloride ($^{103}$RuCl$_3$) having an activity of 960 uCi (spec. activity 310 uCi/umole) were added. The solvent was then removed by passing over nitrogen and gentle heating. After evacuation at approximately 0.13 kPa the ampoule was sealed and heated at 170° C. for 30 minutes. After cooling, the ampoule was opened and the contents were dissolved in chloroform. The solution obtained was then provided on a column having 2 ml of neutral aluminium oxide, and eluted with chloroform to remove the non-converted ruthenium trichloride. The activity of the eluate was 580 uCi. After reducing the volume the eluate was chromatographed on a silica gel plate, using a mixture of acetone and chloroform (10:90 v/v) as the mobile phase. The Rf-value of the ruthenocenoyl ethylglycinate obtained was 0.48, so slightly different from that of the starting ferocenoyl compound (0.43). The total zone having an Rf-value of 0.48 was eluted with chloroform; also acetone and ethanol are suitable. The desired ester was obtained in a yield of 2.1 mg, having a specific activity of 16 uCi/umole.

EXAMPLE II

Preparation of ruthenocenoyl ethylglycinate and 1,1'-bis-(ethylglycinate), labelled with ruthenium-103. In 2 ml of acetone were dissolved 3 mg of rutheniumtrichloride hydrate, 10 mg of ferrocenoyl ethylglycinate and 2 uCi of ruthenium-103 trichloride. After boiling for 90 min. under reflux the solution was chromatographed. By thin layer chromatography two radioactive compounds could be separated, viz. ruthenium-103 labelled ruthenocenoyl ethylglycinate and ruthenocenoyl 1,1'-bis(ethylglycinate) in radiochemical yields of 10.6% and 10.1% respectively.

EXAMPLE III

Preparation of ruthenocenoyl ethylglycinate and 1,1'-bis-(ethylglycinate), labelled with ruthenium-97. To 10 mg of ferrocenoyl ethylglycinate in a 1 ml glass ampoule was added 100 ul of an ethanolic solution of ruthenium-97 trichloride, having an activity of 1 mCi and 100 ul of an ethanolic solution of inactive ruthenium trichloride in a concentration of 2 mg/ml. After dissolving the ferrocenoyl ethylglycinate by gentle heating the solvent was evaporated in vacuo. To the resulting residue was added 100 ul of dimethylformamide and the ampoule was sealed after evacuation. Thereupon the ampoule was heated at 170° C. for 1 hour. After cooling, the contents of the ampoule were dissolved in methylene chloride and chromatographed on a silica gel plate (Merck Fertigplatte) with methylene chloride-ethylacetate 2:1 (v/v) as the mobile phase. By scanning the developed plate with a chromatogram scanner it appeared that 15% of the initial radioactivity was present as labelled ruthenocenoyl ethylglycinate and 20% as labelled ruthenocenoyl 1,1'-bis(ethylglycinate) formula:

[$^{97}$Ru—Rc—(—CO—NH—CH$_2$—COOC$_2$H$_5$)$_2$].

EXAMPLE IV

Preparation of ruthenocenoylglycine, labelled with ruthenium-103; formula: [$^{103}$Ru]—Rc—CO—NH—CH$_2$—COOH. Labelled ruthenocenoyl ethylglycinate, obtained according to Example I, having a spec. activity of 16 uCi/umole was dissolved in an amount corresponding with 5 uCi in 500 ul of ethanol, after which 30 ul of an ethanolic solution of sodiumhydroxide (0.1 g of NaOH per 3 ml of ethanol) were added: the solution was left to stand overnight at ambient temperature. After acidification with 20 ul of 10N hydrochloric acid the solvent was evaporated. After addition of 2 ml of water and 10 ul of 10N hydrochloric acid, the residue was extracted once with 0.5 ml of chloroform to remove small quantities of non-converted ester. To recover the desired ruthenocenoylglycine four extractions each with 1 ml of ethyl acetate were carried out. The product was obtained in an activity yield of 4.2 uCi. After purification by thin-layer chromatography on a silica gel plate with formic acid/acetone/chloroform 5:20:75 (v/v/v) as the mobile phase the pure substance was isolated having a Rf-value of 0.35.

In a corresponding way as described in Examples I and IV osmocenoylglycine, labelled with osmium-191 could be prepared.

EXAMPLE V

Preparation of inactive ruthenocenoylglycine and its ethyl ester.

To a solution of 515 mg of ruthenocenyl carboxylic acid in 30 ml of benzene was added in 30 minutes 410 mg of PCl$_5$ portion-wise, while stirring and flushing with nitrogen. After approximately 2 hours stirring at room temperature the acid chloride obtained was isolated by evaporating benzene and POCl$_3$ in vacuo. The acid chloride was dissolved in tetrahydrofuran and added to a solution of 400 mg of ethylglycinate in 200 ml of tetrahydrofuran. After staying overnight the excess ethylglycinate-HCl salt was filtered off and the filtrate was reduced in vacuo. The residue was purified by column chromatography (Al$_2$O$_3$, chloroform), and further by recrystallization from ethanol. The desired ruthenocenoyl ethylglycinate was obtained in a yield of 620 mg; melting point 162° C.; R$_f$=0.48 (chloroform/acetone=9:1). Elementary analysis: 50.26% C (calculated 50.00), 4.81% H (calculated 4.72), 3.69% N (calculated 3.89).

The above ethylester could be saponified as follows. To ruthenocenoyl ethylglycinate in an amount of 56 mg was added 7 mg sodiumhydroxide in 300 ul of ethanol. After staying overnight the solvent was evaporated and the residue mixed with 500 ul of water; to this mixture diluted hydrochloric acid was slowly added. The crystallized ruthenocenoylglycine was filtered off and recrystallized from a mixture of ethanol and water. Yield 50 mg; melting point 203° C.; R$_f$=0.35 (formic acid/acetone/chloroform—5:20:7). Elementary analysis: 45.30% C (calculated 47.00), 3.73% H (calculated 3.91), 4.19% N (calculated 4.22).

EXAMPLE VI

Use of labelled ruthenocenes for organ distribution studies in mouse and rat.

Ruthenocenoylglycine (Rc glycine) and ruthenocenoyl ethylglycinate (ester) both labelled with ruthenium-103, were injected in mice and rats in dosages of approx. 0.5 umole per kg of body weight. After certain periods of time (see Table A) the distribution of the radioactivity over the organs of the test animals was determined. The results are presented in Table A.

TABLE A

| | | | $^{103}$Ru-organ distribution in mouse and rat. | | |
|---|---|---|---|---|---|
| test animal | radioact. compound | activity after hours | $^{103}$Ru conc. [dose/% body/wt] | | |
| | | | lung | liver | kidney |
| mouse | Rc glycine | 1 | 27 | 58 | 212 |
| | | 3 | 5.6 | 15 | 196 |
| rat | Rc glycine | 3 | 3 | 14 | 59 |
| mouse | Rc glycine ester | 1 | 6 | 43 | 141 |
| | | 3 | 2.6 | 24 | 90 |
| | | 6 | 3.0 | 3.5 | 125 |

The results show that the compounds tested have a good organ specificity with regard to the kidney.

EXAMPLE VII

Renal clearance of labelled ruthenocenoyl compounds determined in rabbits.

Ruthenium-103 labelled ruthenocenoylglycine and 1,1'-diglycine with specific activities of 16 and 80 uCi/umole respectively were used, as well as for the comparative study iodine-125 labelled o-iodohippuric acid sodium acid with a specific activity of 30 uCi/umole. The renal clearance was determined in male rabbits weighing 1.5 to 5.7 kg. The animals were anesthetized with Nembutal ® barbituate. The urinary bladder was catheterized, and catheters were also inserted into the artery and vein of the left and right ear respectively. Three lead shielded NaI (Tl) crystals connected to lead collimators with 1 cm aperatures were positioned on the kidneys and liver for continuous external registration of relative ruthenium-103 activity in these organs. The renal clearance was determined as follows. Infusion of saline at a rate which insures a urine flow of 1.0 to 1.5 ml/min. was started 30 min. before injection of the radioactive material. A mixture of approximately 5 uCi of the ruthenium-103 labelled ruthenocenoyl compounds and 10 uCi of iodine-125 labelled o-iodohippuric acid sodium salt in 1 ml of saline was injected into the vein, and blood samples were drawn from the auricular artery at 1, 2, 4, 8, 15, 30 and 60 minutes after administration. Urine from the bladder was collected at 5 to 10 min. intervals between 5 and 60 minutes after administration. In order to estimate subsequent urinary excretion of residual radioactivity, the test animals were placed in so-called metabolic cages, and 24 hour-urine samples were collected up to 48 hours after that time. Ruthenium-103 and iodine-125 activities in plasma and urine samples were measured by means of a dual channel well-type scintillation counter. Iodine-125 counting rates were corrected for spill-over of ruthenium-103 radiation.

The radioactivity concentrations in plasma (P) were calculated at the midpoint of the time intervals for the different urine collection periods. The clearance at different times after radioactivity injection was calculated according to the formula:

$$\text{clearance (ml/min)} = \frac{U \times V}{P \times t}$$

wherein
U = radioactivity concentration in urine (% dose/ml);
V = urine volume collected in the time interval (ml);
P = radioactivity concentration in plasma (% dose/ml); and
t = time interval (min.)

In the period 0–60 min. after radioactivity injection 7–8 different urine fractions were collected and 7–8 radioactivity concentrations in plasma were measured, therefore 7–8 clearance values could be calculated.

The results are presented in the accompanying FIGS. 1–4. The accumulation of ruthenium-103 labelled ruthenocenoylglycine and ruthenocenoyl-1,1'-diglycine in the kidneys of rabbits, measured with external gamma-detectors, are recorded in FIGS. 1 and 2 respectively. In these figures K means kidney and L means liver. The emitted radiation was measured in cpm. and plotted on the ordinate. Both compounds show a very rapid accumulation in the kidneys followed by a rapid excretion.

The clearance of ruthenium-103 labelled ruthenocenoylglycine was compared with that of iodine-125 labelled o-iodohippuric acid sodium salt. After simultaneous injection of the radioactive compounds in rabbits the ruthenium-103 and iodine-125 contents were measured in urine and plasma. The two compounds could be compared by calculating the ratio:clearance ruthenium-103/clearance iodine-125. When the renal clearance of both compounds is equally effective this ratio = 1.

Figure 3:
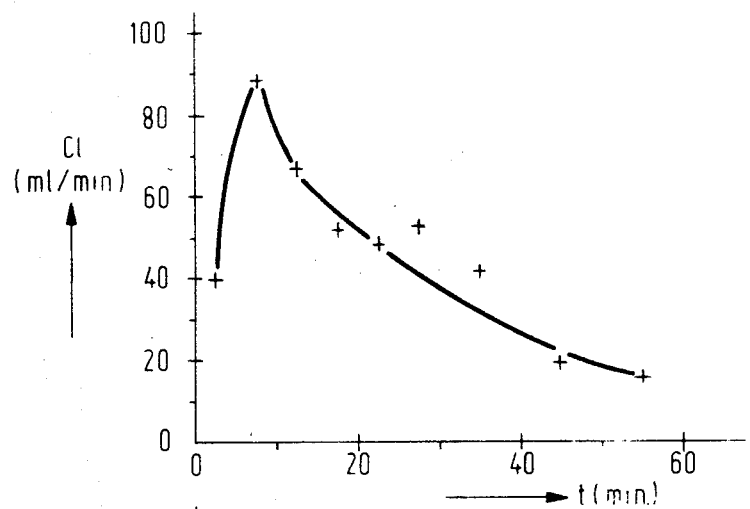
Figure 4:
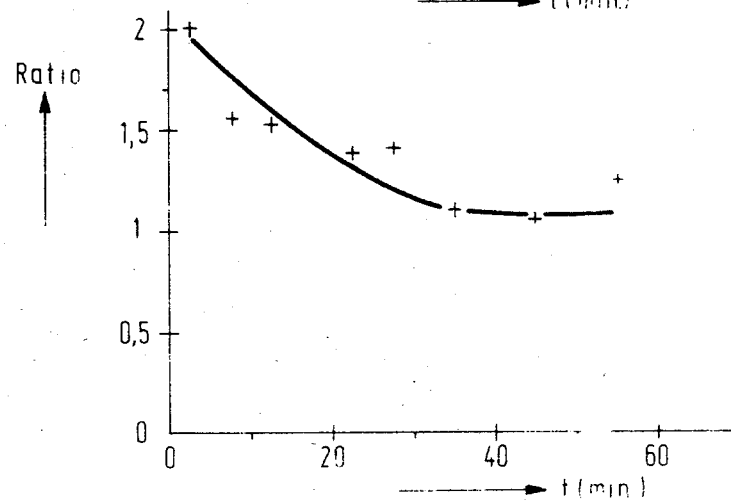

In FIG. 3 the renal clearance (Cl) in ml/min. for labelled ruthenocenoylglycine is plotted against time. In FIG. 4 the above-defined ratio is plotted against time. From FIG. 4 it is clear that within the first 30 minutes after injection ruthenium-103 labelled ruthenocenoyl glycine is cleared more rapidly than iodine-125 labelled o-iodohippuric acid sodium salt. After 30 minutes iodine-125 iodohippuric acid salt is eliminated to the same extent as labelled ruthenocenoylglycine.

EXAMPLE VIII

The renal clearance by tubular excretion is a measure for the renal function was determined in two dogs, viz. beagles with body weights of 13.8 kg (dog a) and 14.8 kg (dog b) respectively by the generally recognized single injection method, in broad outline as described in Example VII. As radioactive materials were used iodine-131 labelled o-iodohippuric acid sodium salt (I-131 Hippuran), indium-111 DTPA (diethylene triamine pentaacetic acid) and ruthenium-97 labelled ruthenocenoylglycine. Indium-111DTP is also recommended to be used in radiodiagnostic compositions for examination of the renal glomerular filtration function. The time intervals between the various administrations were chosen in such a way, that no interference between the radioactive materials could occur. The radioactive materials were administered intraveneously, blood samples were collected 5, 10, 15, 30, 60 and 90 minutes after administration. The emitted radioactivity was determined with a gamma camera. The decreasing radioactivity of the successive blood samples is a measure for the elimination of the radioactive compound from the blood. From these results the clearance values could be calculated. The clearance values are presented in Table B.

TABLE B

| Clearance of radioactive compounds after administration to dogs | | |
|---|---|---|
| dog | radioactive compound | clearance (ml/min) |
| a | I - 131 Hippuran | 169.7 |
| | In - 111 DTPA | 79.6 |
| | Ru-97 ruthenocenoylglycine | 191.6 |

| Clearance of radioactive compounds after administration to dogs | | |
|---|---|---|
| dog | radioactive compound | clearance (ml/min) |
| b | I - 131 Hippuran | 170.8 |
|  | In - 111 DTPA | 62.2 |
|  | Ru-97 ruthenocenoylglycine | 218.7 |

The above results show, that the clearance of the radiolabelled ruthenocenoylglycine is faster than that of labelled o-iodohippuric acid salt; the clearance of indium-111 DTPA is comparatively slow. The images obtained with the gamma camera unambiguously show that the labelled ruthenocenoylglycine is eliminated from the blood only through the kidneys.

EXAMPLE IX

In the previous Examples VI–VIII inactive ruthenocenoylglycine and derivatives thereof were used as inactive carriers or loads. Also other substances, however, are suitable as inactive carriers, provided that these substances have a fast renal clearance.

In the following experiments ruthenocenoylglycine was replaced by ferrocenoylglycine as inactive carrer or load. Mice were injected with ruthenium-103 labelled ruthenocenoylglycine, to which inactive ruthenocenoylglycine (first series of experiments) or ferrocenoylglycine (second series of experiments) respectively in doses increasing from 0.1 to 430 umole per kg body weight was added. The percentages of ruthenium-103 excreted with the urine was in both series approximately the same. The concentration of ruthenium-103 (% dose/% weight) was in both series approximately the same in the following organs: urine, blood, liver and muscle. The concentration of ruthenium-103 (% does/% weight) in the kidneys depends strongly on the dose, but has for the same doses equal values in both series.

Figure 5:
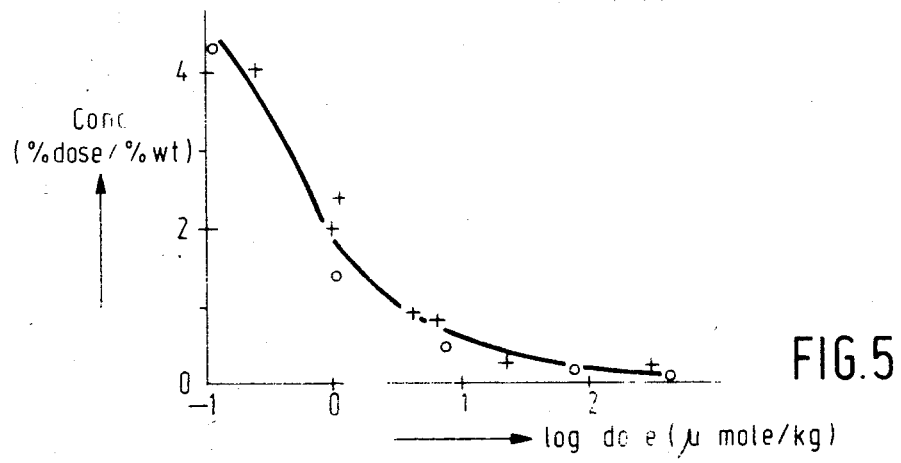

The results are shown in FIG. 5, wherein the concentration of ruthenium-103 in the kidneys (% dose/% weight) is plotted against the logarithm of the dose of inactive carrier (umole/kg). The results obtained with inactive rutheniumglycine as carrier are presented as circles, the results with ferrocenoylglycine as plussigns.

The last results indicate that the presence of sufficient inactive carrier is indispensable for determining the renal function.

Comparable results were obtained when instead of inactive ruthenocenoyl- or ferrocenoylglycine ortho-iodohippuric acid (salt) or para-aminohippuric acid (salt) are used as inactive carriers.

What is claimed:

1. Radiolabelled metallocene derivatives of the general formula

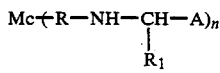

wherein
Mc is a metallocenyl group with a radioactive central atom,
R is a carbonyl or methylene group,
$R_1$ is a hydrogen atom or an alkyl group having 1–4 carbon atoms,
A is a carboxy group or a pharmaceutically acceptable salt thereof, or an alkoxycarbonyl or alkanoyl group having 2–5 carbon atoms, and
n is 1–4.

2. Radiolabelled metallocene derivatives as claimed in claim 1, comprising radionuclides of metals suitable for the formation of metallocenes, including iron, ruthenium, osmium, chromium, canadium, or cobalt, as central atoms.

3. Radiolabelled metallocene derivatives as claimed in claim 2, comprising ruthenium-97 as central atom.

4. Radiolabelled metallocene derivatives as claimed in claim 3, having the general formula

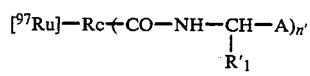

wherein
$[^{97}Ru]$—Rc is ruthenocenyl radiolabelled with ruthenium-97,
A is a carboxy group or a pharmaceutically acceptable salt thereof, or an alkoxycarbonyl or alkanoyl group having 2–5 carbon atoms,
$R'_1$ is a hydrogen atom or a methyl group, and
$n'$ is 1 or 2.

5. Radiolabelled metallocene derivatives as claimed in claim 4, selected from the group consisting of ruthenium-97 labelled ruthenocenoylglycine and 1,1'-diglycine.

6. A method of preparing radiolabelled metallocene derivatives having the following general formula

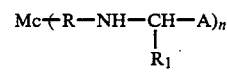

wherein
Mc is a metallocenyl group having a radioactive central atom,
R is a carbonyl or methylene group,
$R_1$ is a hydrogen atom or an alkyl group having 1–4 carbon atoms,
A is a carboxy group or a pharmaceutically acceptable salt thereof, or an alkoxycarbonyl or alkanoyl group having 2–5 carbon atoms,
and n is 1–4,
comprising reacting a non-radioactive metallocene derivative with a radioactive metal compound.

7. Radiodiagnostic compositions, to be used particularly for examining the renal function, comprising a pharmaceutically acceptable formulation liquid and, if desired, inactive carriers, and auxiliary substances, and a radiolabelled metallocene derivatives of the general formula

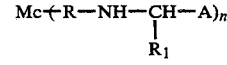

wherein
Mc is a metallocenyl group with a radioactive central atom,
R is a carbonyl or methylene group,
$R_1$ is a hydrogen atom or an alkyl group having 1–4 carbon atoms,
A is a carboxy group or a pharmaceutically acceptable salt thereof, or an alkoxycarbonyl or alkanoyl group having 2–5 carbon atoms, and n is 1–4.

8. Radiodiagnostic compositions as claimed in claim 7, containing an inactive carrier having a fast renal clearance selected from the group consisting of inactive metallocenes having the general formula

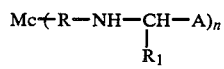

wherein
Mc is a non-radioactive metallocenyl group,
R is a carbonyl or methylene group,
$R_1$ is a hydrogen atom or an alkyl group having 1-4 carbon atoms,
A is a carboxy group or a pharmaceutically acceptable salt thereof, or an alkoxycarbonyl or alkanoyl group having 2-5 carbon atoms
and n is 1-4,
and substituted for unsubstituted hippuric acid derivatives.

9. Radiodiagnostic compositions as claimed in claim 7, comprising radiolabelled metallocene derivatives having radionuclides of metals suitable for the formation of metallocenes, selected from the group of iron, ruthenium, osmium, chromium, vanadium, or coblat, as central atoms.

10. Radiodiagnostic compositions as claimed in claim 9, comprising radiolabelled metallocene derivatives having ruthenium-97 as central atom.

11. Radiodiagnostic compositions as claimed in claim 10, comprising radiolabelled metallocene derivatives having the general formula

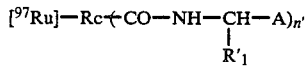

wherein
$[^{97}Ru]$—Rc is ruthenocenyl radiolabelled with ruthenium-97,
A is a carboxy group or a pharmaceutically acceptable salt thereof, or an alkoxycarbonyl or alkanoyl group having 2-5 carbon atoms,
$R_1$ is a hydrogen atom or a methyl group and
$n^1$ is 1 or 2.

12. Radiodiagnostic compositions as claimed in claim 11, comprising metallocene derivatives selected from the group consisting of ruthenium-97 labelled ruthenocenoylglycine and 1,1'-diglycine.

13. Inactive ruthenocene derivatives of the general formula

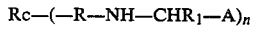

wherein
Rc is a ruthenocenyl group,
R is a carbonyl or methylene group,
$R_1$ is a hydrogen atom or an alkyl group having 1-4 carbon atoms,
A is a carboxy group or a pharmaceutically acceptable salt thereof, or an alkoxycarbonyl or alkanoyl group having 2-5 carbon atoms, and
n is 1-4.

14. Radiodiagnostic compositions as claimed in claim 8, comprising radiolabelled metallocense derivatives having radionuclides of metals suitable for the formation of metallocenes, selected from the group of iron, ruthenium, osmium, chromium, vanadium, or cobalt, as central atoms.

15. Radiodiagnostic compositions as claimed in claim 14, comprising radiolabelled metallocene derivatives having ruthenium-97 as central atom.

16. Radiodiagnostic compositions as claimed in claim 15, comprising radioabelled metallocene derivatives having the general formula

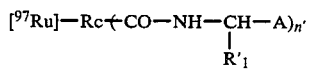

wherein
$[^{97}Ru]$—Rc is ruthenocenyl radiolabelled with ruthenium-97,
A is a carboxy group or a pharmaceutically acceptable salt thereof, or an alkoxycarbonyl or alkanoyl group having 2-5 carbon atoms,
$R'_1$ is a hydrogen atom or a methyl group, and
$n'$ is 1 or 2.

17. Radiodiagnostic compositions as claimed in claim 16, comprising metallocene derivatives selected from the group consisting of ruthenium-97 labelled ruthenocenoylglycine and 1,1'-diglycine.

18. Radiodiagnostic compositions as claimed in claims 8, 9, 10, 11 or 12, wherein the inactive carrier is a metallocene derivative of the general formula

wherein
Rc is a ruthenocenyl group
R is a carbonyl or methylene group,
$R_1$ is a hydrogen atom or an alkyl group having 1-4 carbon atoms,
A is a carboxy group of a pharmaceutically acceptable salt thereof, or an alkoxycarbonyl or alkanoyl group having 2-5 carbon atoms, and
n is 1-4.

19. A method of performing a radiodiagnostic examination in a warm-blooded living being comprising administering a radiodiagnostic composition comprising a pharmaceutically acceptable formulation liquid and a radiolabelled metallocene derivative of the general formula

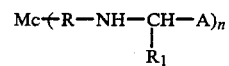

wherein
Mc is a metallocenyl group with a radioactive central atom,
R is a carbonyl or methylene group,
$R_1$ is a hydrogen atom or an alkyl group having 1-4 carbon atoms,
A is a carboxy group or a pharmaceutically acceptable salt thereof, or an alkoxycarbonyl or alkanoyl group having 2-5 carbon atoms and
n is 1-4.

20. A method according to claim 19 wherein said composition contains an inactive carrier having a fast renal clearance selected from the group consisting of inactive metallocenes having the general formula

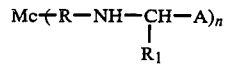

wherein
- Mc is a non-radioactive metallocenyl group with a radioactive central atom,
- R is a carbonyl or methylene group,
- $R_1$ is a hydrogen atom or an alkyl group having 1–4 carbon atoms,
- A is a carboxy group or a pharmaceutically acceptable salt thereof, or an alkoxycarbonyl or alkanoyl group having 2–5 carbon atoms, and
- n is 1–4 and substituted or unsubstituted hippuric acid derivatives.

21. A method according to claim 19 wherein said radioactive central atom is selected from the group consisting of iron, ruthenium, osmium, chromium, vanadium and cobalt.

22. A method according to claim 21 wherein said central atom is ruthenium-97.

23. A method according to claim 22 wherein the radiolabelled metallocene derivatives have the general formula

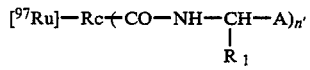

wherein

- [$^{97}$Ru]—Rc is ruthenocenyl radiolabelled with ruthenium-97,
- A is a carboxy group or a pharmaceutically acceptable salt thereof, or an alkoxycarbonyl or alkanoyl group having 2–5 carbon atoms,
- $R'_1$ is a hydrogen atom or a methyl group, and
- $n'$ is 1 or 2.

24. A method according to claim 23 wherein the metallocene derivative is selected from the group consisting of ruthenium-97 labelled ruthenocenoylglycine and 1,1'-diglycine.

25. A method as claimed in claims 20, 21, 22, 23 or 24 wherein the inactive carrier is a metallocene derivative of the general formula

wherein
- Rc is a ruthenocenyl group
- R is a carbonyl or methylene group,
- $R_1$ is a hydrogen atom or an alkyl group having 1–4 carbon atoms,
- A is a carboxy group or a pharmaceutically acceptable salt thereof, or an alkoxycarbonyl or alkanoyl group having 2–5 carbon atoms, and
- n is 1–4.

26. A method as claimed in claims 20, 21, 22, 23 or 24 wherein the composition is administered in a quantity from 0.5 to 2 mCi per 70 kg of body weight.

* * * * *